(12) United States Patent
Yarborough et al.

(10) Patent No.: US 7,467,482 B2
(45) Date of Patent: Dec. 23, 2008

(54) METHOD FOR LYOPHILIZING AN ACTIVE AGENT

(75) Inventors: Cody L. Yarborough, Ft. Collins, CO (US); Dominic G. Madril, Loveland, CO (US); Rajan Bawa, Ft. Collins, CO (US)

(73) Assignee: QLT USA, Inc., Fort Collins, CO (US)

( * ) Notice: Subject to any disclaimer, the term of this patent is extended or adjusted under 35 U.S.C. 154(b) by 24 days.

(21) Appl. No.: 11/099,919

(22) Filed: Apr. 6, 2005

(65) Prior Publication Data

US 2005/0193586 A1  Sep. 8, 2005

Related U.S. Application Data

(60) Continuation of application No. 10/391,480, filed on Mar. 17, 2003, now Pat. No. 6,907,679, which is a continuation-in-part of application No. 09/909,671, filed on Jul. 20, 2001, now Pat. No. 6,722,054, which is a division of application No. 09/190,341, filed on Nov. 12, 1998, now abandoned.

(51) Int. Cl.
*F26B 5/06* (2006.01)

(52) U.S. Cl. .......................... 34/287; 34/237; 436/177; 436/174

(58) Field of Classification Search ................. 34/285, 34/287, 237, 284, 296; 215/305; 206/439, 206/367.1; 422/942; 536/21
See application file for complete search history.

(56) References Cited

U.S. PATENT DOCUMENTS

| | | | |
|---|---|---|---|
| 3,454,178 A | 7/1969 | Bender et al. | |
| 3,810,469 A | 5/1974 | Hurschman | |
| 4,060,911 A | 12/1977 | Weiler et al. | |
| 4,172,457 A | 10/1979 | Choksi et al. | |
| 4,286,389 A | 9/1981 | Ogle | |
| 4,306,357 A | 12/1981 | Villarejos | |
| 4,501,719 A | 2/1985 | Williams | |
| 4,521,975 A | 6/1985 | Bailey | |
| 4,729,208 A | 3/1988 | Galy et al. | |
| 4,758,230 A | 7/1988 | Rycroft | |
| 4,829,006 A | 5/1989 | Smith et al. | |
| 4,872,572 A | 10/1989 | Schrooten | |
| 4,952,208 A | 8/1990 | Lix | |
| 5,005,721 A | 4/1991 | Jordan | |
| 5,320,603 A * | 6/1994 | Vetter et al. | 604/82 |

(Continued)

OTHER PUBLICATIONS

"U.S. Appl. No. 09/190,341 Advisory Action mailed Feb. 11, 2002", 2 pgs.

(Continued)

*Primary Examiner*—Kenneth B Rinehart
(74) *Attorney, Agent, or Firm*—Schwegman, Lundberg & Woessner, P.A.

(57) ABSTRACT

A process for lyophilizing a solution of an active agent in a container is provided. Solution of active agent is deposited into a container, the container is covered with a covering plate and placed inside a lyophilizing apparatus. Lyophilization can be conducted to dryness by radiation, convection or both. Also provided is a device made by this process, an active agent-plastic administration device (e.g., a syringe), containing an active agent in the form of lyophilized cake, and an array of such administration devices.

19 Claims, 8 Drawing Sheets

U.S. PATENT DOCUMENTS

| | | | |
|---|---|---|---|
| 5,334,162 | A | 8/1994 | Harris |
| 5,519,984 | A | 5/1996 | Beussink et al. |
| 5,770,559 | A | 6/1998 | Manning et al. |
| 5,779,668 | A | 7/1998 | Grabenkort |
| 5,803,284 | A | 9/1998 | Grimard |
| 5,807,345 | A | 9/1998 | Grabenkort |
| 5,819,964 | A | 10/1998 | Grimard |
| 5,882,603 | A | 3/1999 | Taggart |
| 5,916,526 | A | 6/1999 | Robbins |
| 6,027,694 | A | 2/2000 | Boulton et al. |
| 6,083,761 | A | 7/2000 | Kedar et al. |
| 6,136,273 | A | 10/2000 | Seguin et al. |
| 6,164,044 | A | 12/2000 | Porfano et al. |
| 6,189,292 | B1 | 2/2001 | Odell et al. |
| 6,199,297 | B1 | 3/2001 | Wisniewski |
| 6,224,883 | B1 | 5/2001 | Roskos et al. |
| 6,241,949 | B1 | 6/2001 | Kane |
| 6,340,589 | B1 | 1/2002 | Turner et al. |
| 6,436,351 | B1 | 8/2002 | Gubernator et al. |
| 6,566,144 | B1 | 5/2003 | Madril et al. |
| 2001/0037091 | A1 | 11/2001 | Wironen et al. |
| 2001/0042317 | A1 | 11/2001 | Yarborough et al. |

OTHER PUBLICATIONS

"U.S. Appl. No. 09/190,341 Final office action mailed Oct. 9, 2001", 8 pgs.

"U.S. Appl. No. 09/190,341 Final office action mailed Oct. 15, 2002", 8 pgs.

"U.S. Appl. No. 09/190,341 Non Final office action mailed Apr. 9, 2003", 10 pgs.

"U.S. Appl. No. 09/190,341 Non Final office action mailed May 23, 2001", 23 pgs.

"U.S. Appl. No. 09/190,341 Non Final office action mailed May 29, 2002", 7 pgs.

"U.S. Appl. No. 09/190,341 Resonse filed Jan. 14, 2003 to Final office action mailed Oct. 15, 2002", 11 pgs.

"U.S. Appl. No. 09/190,341 Respone filed Jul. 27, 2001 to Non Final office action mailed May 23, 2001", 6 pgs.

"U.S. Appl. No. 09/190,341 Response filed Jul. 18, 2002 to Non Final office action mailed May 29, 2002", 4 pgs.

"U.S. Appl. No. 09/909,671 Final office action mailed Apr. 8, 2003", 5 pgs.

"U.S. Appl. No. 09/909,671 Non Final office action mailed Aug. 16, 2002", 8 pgs.

"U.S. Appl. No. 09/909,671 Notice of allowance mailed Jun. 25, 2003", 6 pgs.

"U.S. Appl. No. 09/909,671 Notice of allowance mailed Nov. 14, 2003", 6 pgs.

"U.S. Appl. No. 09/909,671 Response filed Jan. 9, 2003 to Non Final office action mailed Aug. 16, 2002", 11 pgs.

"U.S. Appl. No. 09/909,671 Response filed Jun. 4, 2003 to Final office action mailed Apr. 8, 2003", 3 pgs.

"U.S. Appl. No. 10/391,480 Non final office action mailed Apr. 7, 2004", 12 pgs.

"U.S. Appl. No. 10/391,480 Notice of allowance mailed Feb. 4, 2005", 5 pgs.

"U.S. Appl. No. 10/391,480 Notice of allowance mailed Jul. 22, 2004", 5 pgs.

"U.S. Appl. No. 10/391,480 Response filed Jun. 16, 2004 to Non final office action mailed Apr. 7, 2004", 6 pgs.

* cited by examiner

METHOD FOR LYOPHILIZING AN ACTIVE AGENT

RELATED APPLICATIONS

This application is a continuation of U.S. patent application Ser. No. 10/391,480, filed Mar. 17, 2003 now U.S. Pat. No. 6,907,679, which is a continuation-in-part of U.S. patent application Ser. No. 09/909,671, filed Jul. 20, 2001 now U.S. Pat. No. 6,722,054, which is a divisional of U.S. patent application Ser. No. 09/190,341, filed Nov. 12, 1998 now abandoned, which are incorporated herein by reference.

BACKGROUND

Lyophilization is a process which extracts liquid from a solution to form a granular solid or powder which is stable and easier to store at room temperature than the liquid. Lyophilization is carried out by freeze drying, or, more specifically, freezing followed by sublimation, which is the transition of a solid to the gaseous state without first passing through an intermediate liquid phase. Lyophilization is used instead of simply filling a container, such as a syringe, with a solid form of the active agent, because existing powder-filling equipment is incapable of filling to the precise tolerances required for some potent active agents, including various pharmaceuticals. The lyophilization process allows a larger quantity by weight of the active agent and solvent to be filled in the container, thereby allowing for greater accuracy than powder-filling.

Lyophilization has many advantages compared to other drying and preserving techniques. It maintains the quality of the preserved substance, because the substance remains at a temperature that is below the freezing-point during sublimation. The resulting lyophilized matter is usually stored without refrigeration, reducing storage and transportation costs of the substance as well as the storage space required for the product. It also reduces the weight of the lyophilized product, which similarly reduces shipping and related costs. In addition, lyophilized substances are easily reconstituted prior to use, often in the very containers in which they were lyophilized and stored.

Lyophilization is particularly useful for preserving and storing various pharmaceuticals, because it increases their shelf-life. For example, when the lyophilization is performed in a syringe, the lyophilized medication can be stored in the syringe. Diluent is then added to the syringe for reconstitution of the medication, and the medication is administered from the syringe to the patient.

Lyophilization has traditionally been performed in glass vials or ampules, but not syringes. Syringes, however, are the preferable means for lyophilization for active agents whose ultimate use will be from a syringe, since the active agent can be reconstituted and ultimately used in the syringe in which it was lyophilized. Lyophilization in a vial or ampule, on the other hand, requires transfer of the reconstituted active agent from the vial or ampule to the syringe. A particularly useful application for lyophilization in syringes would be for injectable pharmaceuticals.

Although lyophilization in syringes is known, as discussed and disclosed in U.S. Pat. Nos. 5,320,603, 5,184,450, 5,080,649, 4,874,381 and European Patent Application No. 0664137A2, there are problems and drawbacks with the known techniques. As discussed in U.S. Pat. No. 5,320,603, there are generally two types of syringes for lyophilization. A first type syringe for one-time use contains the lyophilized medication to which diluent is added to make the drug injectable. An example of such a syringe is disclosed in European Patent Application No. 0664137A2.

A second type of syringe contains two pistons, namely, a front or distal piston which separates the syringe barrel interior into two chambers, one containing the lyophilized medication and the other containing the diluent. This piston permits the bypass by axial displacement of diluent from one chamber to the other. The contents are mixed, and the second rear or proximal plunger-type piston is used to expel and dispense the reconstituted drug. Examples of this type of syringe are disclosed in U.S. Pat. Nos. 5,320,603 and 4,874,381.

As pointed out in U.S. Pat. No. 5,320,603, in both systems the syringe is prepared by filling the syringe barrel with a quantity of the medication in solvent to be lyophilized. The distal end of the syringe barrel is capped to maintain sterility. The proximal end contains a piston or plunger, which allows the passage and escape of vapor during lyophilization. The syringe is lyophilized to drive off the vaporized solvent, which escapes through the distal end of the syringe barrel. The syringe is then ready for reconstitution with diluent prior to administration of the medication.

These disposable syringes are not readily susceptible to mass production, because they are costly to produce by the known methods. The known production methods generally require the use of many steps, special equipment, or both, as illustrated by U.S. Pat. No. 5,184,450. Regardless of the cost, current production is also difficult because of problems associated with capping the distal end of the syringe during lyophilization to preserve sterility.

In addition, although methods for lyophilization in plastic, as well as glass, syringes, is known, such as disclosed in European Patent Application No. 0664137A2A, there is no current commercial use, of plastic syringes for lyophilization of medication. Glass syringes do not lend themselves as especially practical active agent delivery devices. The preferable means for administering injectable active agents, including pharmaceuticals, is by plastic syringe, which has many advantages over a glass syringe. Most notably, plastic syringes are cheaper, lighter, easier to use and safer than glass syringes.

One reason plastics are not used for such commercial lyophilization is because plastics are less suitable for lyophilization containers than glass. Significantly, the thermal stresses associated with the cooling process of lyophilization limit the capability of some plastics to withstand the process, and these plastics tend to become brittle at temperatures at which glass remains intact. Consequently, lyophilization is rarely performed using plastic. It would be desirable to achieve lyophilization in plastic syringes if this problem could be overcome.

In one option, lyophilization is mass produced by using pre-sterilized, pre-packaged plastic syringes which do not require any special plunger or any other unique syringe configuration to accommodate the lyophilization process. It is desired to use the same type of syringe for the lyophilization method as is used for the administration of pharmaceuticals generally. In addition, by using a standard type of syringe, which is produced in an array of pre-sterilized and pre-packaged syringes on a plastic rack in a plastic tub, the entire tub can be put directly into a lyophilizing apparatus for lyophilization, thereby lending itself to mass production.

Moreover, whereas lyophilization is typically performed by conduction, it is desired to increase the ease and production efficiency of lyophilization by performing it by radiation, convection or both. It has not been shown that a container containing a substance to be lyophilized can be suspended within a lyophilizing apparatus, above and not in contact with any cooling surface of the lyophilizing apparatus. Lyophilization by such means would occur by radiation, convection or both. Lyophilization by radiation, convection, or both, would be easier than lyophilization by conduction, because lyophilization by the former methods is performed by simply loading a container into a tub which is in turn placed into a lyophilizing apparatus. Lyophilization by conduction, however, requires manually placing the container into the lyophilizing apparatus.

These and other advantages of the present invention will become apparent by referring to the detailed description of the preferred embodiment herein.

SUMMARY

The various embodiments described herein relate to a method for lyophilizing an active agent. The teachings provided herein solve the earlier mentioned problems and other problems not stated herein.

The present invention provides a method for lyophilizing a solution, the method comprising depositing the solution into one or more containers and positioning a covering plate comprising one or more protuberances projecting from a surface to align with an opening of the one or more containers. The one or more protuberances are adapted to fit inside at least a portion of the one or more containers. The method generally involves covering the one or more containers with the covering plate before placing the one or more containers and the covering plate inside a lyophilizing apparatus or covering the one or more containers with the covering plate after placing the one or more containers and the covering plate inside the lyophilizing apparatus. The one or more projecting protuberances engage inside at least a portion of the one or more containers. The solution is at least partially lyophilized by cooling the solution and applying a vacuum to the solution. At least partially lyophilizing the solution allows vapor to escape through an annular gap between each of the one or more protuberances and a side wall of each of the one or more containers.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents. Various embodiments are illustrated by way of example and not by way of limitation in the figures of the accompanying drawings in which like references indicate similar elements.

DETAILED DESCRIPTION

In the following detailed description, reference is made to the accompanying drawings which form a part hereof, and in which is shown by way of illustration specific embodiments in which the invention can be practiced. These embodiments are described in sufficient detail to enable those skilled in the art to practice the invention, and it is to be understood that other embodiments can be utilized and that structural changes can be made without departing from the scope of the invention. Therefore, the following detailed description is not to be taken in a limiting sense, and the scope of the subject matter of this application is defined by the appended claims and their equivalents.

Figure 1:
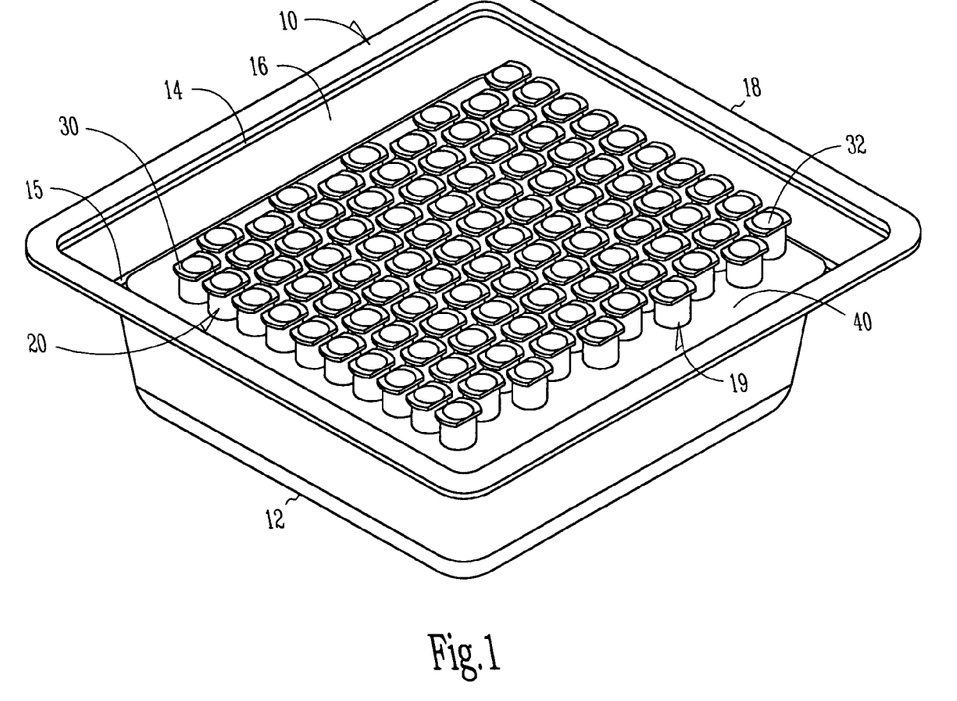
FIG. 1 is a perspective view of a plurality of suspended syringes in a tub as provided in accordance with one embodiment.

In one embodiment, a container 19 includes a single enclosed compartment or multiple enclosed compartments in a tub 10. An example of the container 19 is a syringe 20. FIG. 1 illustrates a plurality of syringes 20, each of which are removable from the tub 10. The tub 10 includes a top 18 and a bottom 12 made into a variety of shapes (e.g., square, rectangular) from a variety of materials (e.g., plastic). In one option, a first ledge 14 extends around an inside 16 periphery of the top 18 of the tub 10 and a second ledge 15 extends around the inside 16 parallel to and below the first ledge 14 of the tub 10. A removable rack 40 is in contact with the second ledge 15 in the tub 10 and is adapted to suspend one or more containers 19 (e.g., syringe) in the tub 10. In one option, the rack 40 secures each removable syringe 20 in a suspended upright position such that an opening 32 of the proximal end 30 of each syringe 20 faces toward the top 18 of the tub 10. The removable rack 40 includes a variety of materials (e.g., plastic). The plurality of removable syringes 20, in one option, are received pre-packaged and pre-sterilized in the tub 10. An example of such an array of syringes 20 include an array of pre-packaged, pre-sterilized, plastic syringes 20 manufactured by Becton Dickinson and Company in what is known as a "Hypak" configuration and disclosed in U.S. Pat. No. 4,758,230.

Figure 2:
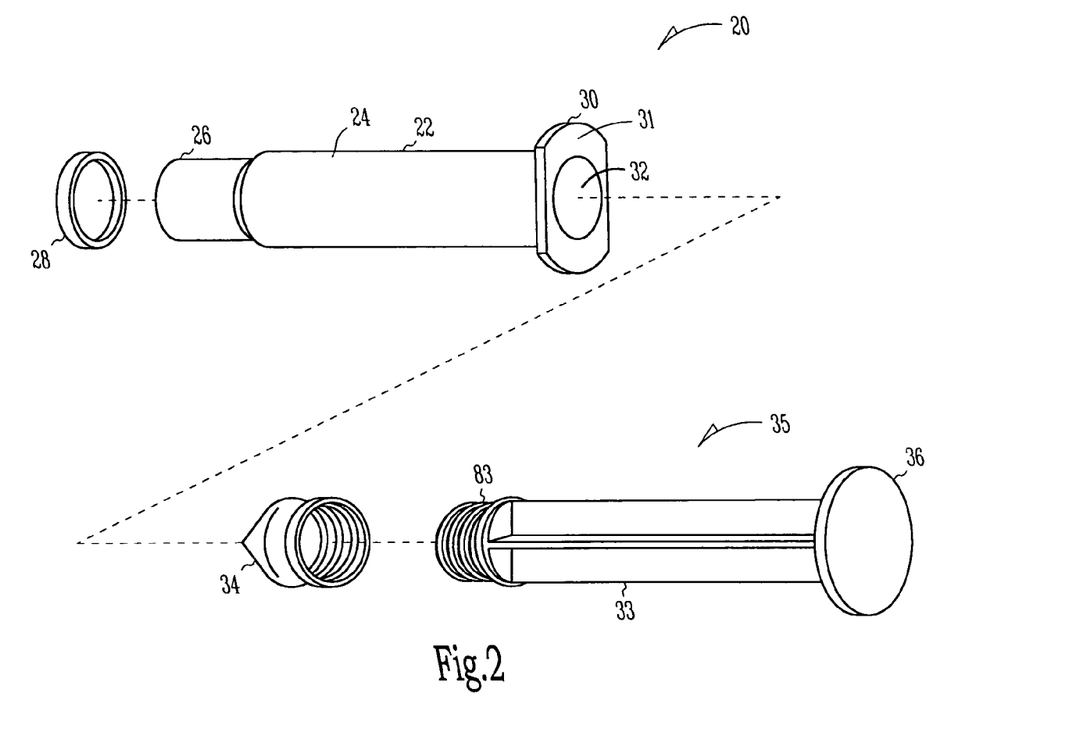
FIG. 2 is a perspective view of a syringe as provided in accordance with one embodiment.

FIG. 2 illustrates one embodiment of syringe 20. Each syringe 20 includes a syringe barrel 22, within which is a chamber 24 for retaining fluid. A distal end 26 of the syringe barrel 22 is capped with a syringe cap 28. The proximal end 30 of the syringe barrel 22 includes the opening 32 which in one option accepts a plunger 35, including a plunger tip 34 and a plunger rod 33. In one option, the plunger tip 34 is screwed onto a threaded end 83 of the plunger rod 33. The plunger tip 34 is moved within the syringe barrel 22 when the plunger rod 33 is pulled by the plunger head 36 toward the proximal end 30 of the syringe barrel 22 or pushed toward the distal end 26 of the syringe barrel 22. The plunger head 36 mates with a syringe flange 31 when pushed towards the distal end 26 of the syringe barrel 22. In one option, the plunger tip 34 and the plunger 35 are removed from the syringe barrel 22. In another option, the syringe barrel 22 is configured to have a smaller diameter toward the distal end 26 of the syringe barrel 22 and a larger diameter toward the proximal end 30 of the syringe barrel 22. In yet another option, the syringe barrel 22 includes a bevel.

Figure 3:
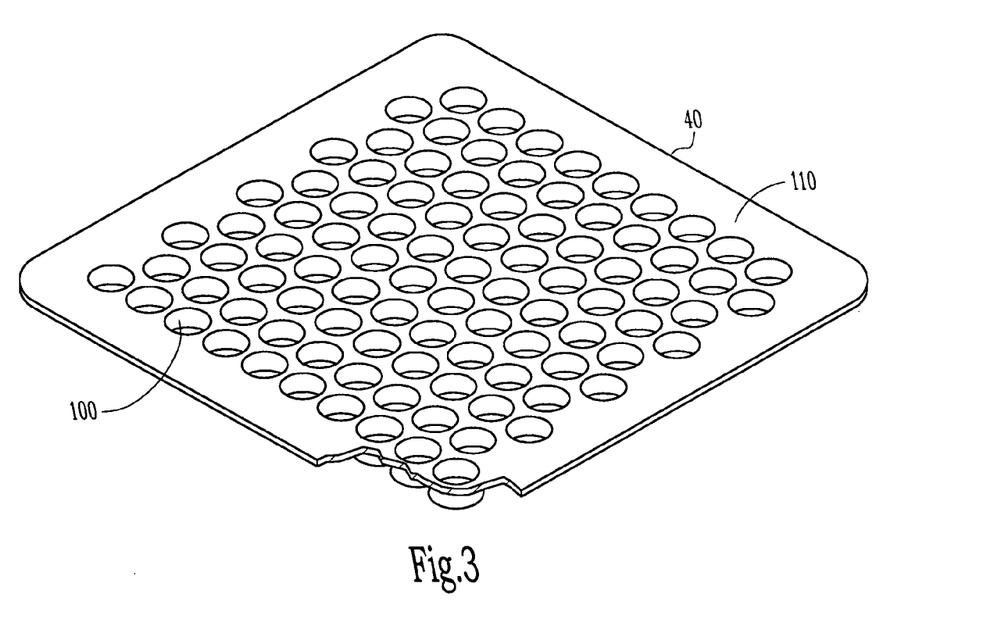
FIG. 3 is a partial cut-away view of a rack as provided in accordance with one embodiment.

The removable rack 40 is shown in FIG. 3. In one option, the rack 40 is fixed about the inside 16 periphery of the tub 10. The rack 40 includes a variety of shapes (e.g., square, rectangular, circular) adapted to fit the shape of the tub 10. The rack 40 includes a plurality of sleeves 100 which houses the syringe barrel 22 of each syringe 20 (See FIG. 1). Each removable syringe 20 is secured in a suspended upright position such that the opening 32 of the proximal end 30 of each syringe 20 faces toward the top 18 of the tub 10 and the distal end 26 of each syringe 20 faces toward the bottom 12 of the tub 10 (See FIG. 1). In one option, the smaller diameter of the syringe barrel 22 toward the distal end 26 communicates and passes through the sleeve 100 of the rack 40. The larger diameter of the syringe barrel 22 toward the proximal end 30 communicates with a top 110 of the rack 40 preventing the syringe 20 from passing entirely through the sleeve 100 thereby securing the syringe 20 in a suspended upright position. In another option, the bevel of the syringe barrel 22 further prevents the syringe 20 from passing entirely through the sleeve 100 securing the syringe 20 in a suspended upright position. In another option, the sleeve 100 is beveled allowing a portion of the syringe 20 with at least one diameter to communicate with and pass through the sleeve 100 of the rack 40 securing the syringe 20 in a suspended upright position.

Figure 4:
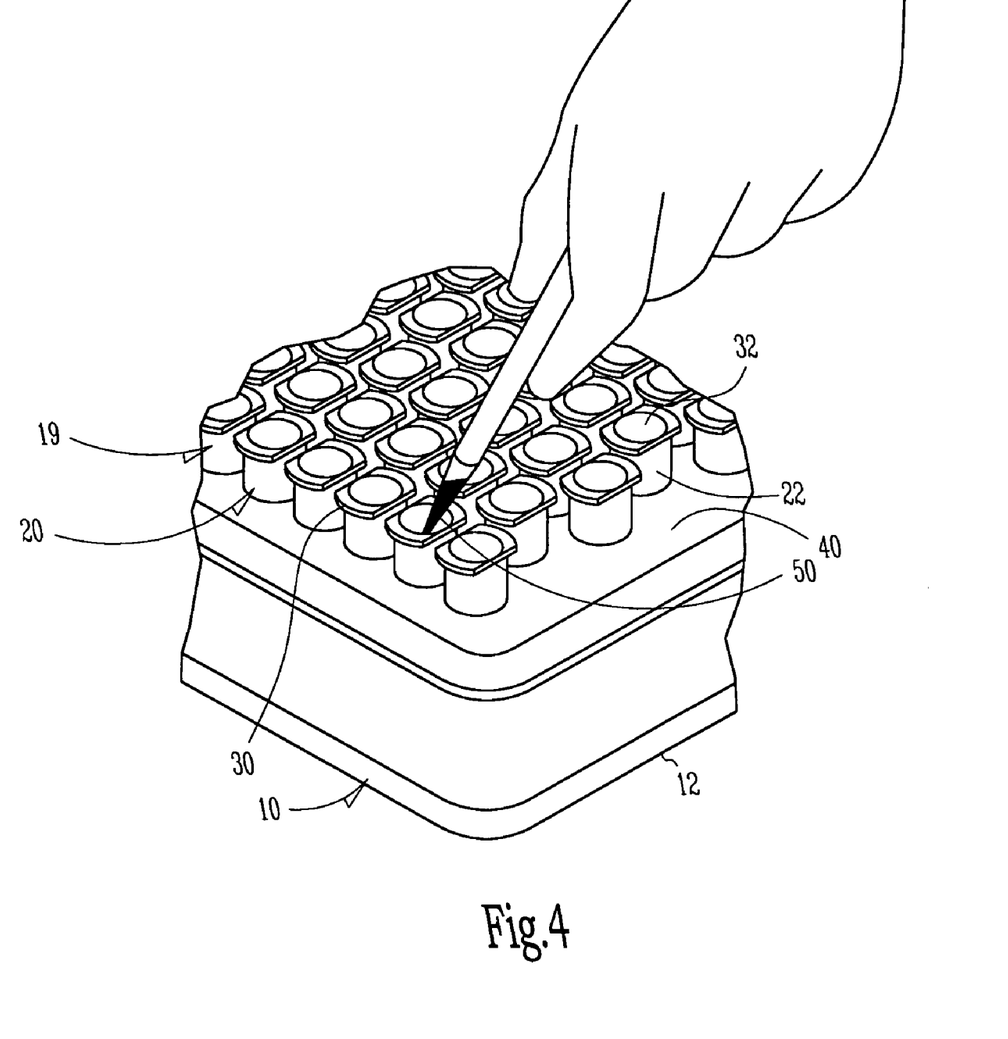
FIG. 4 is a partial cut-away view of a plurality of suspended syringes in a tub and a solution being inserted into one syringe as provided in accordance with one embodiment.

FIG. 4 illustrates one embodiment where each container 19 is loaded vertically into the rack 40 in the tub 10, so a solution 50 (e.g., pharmaceutical) faces the bottom 12 of the tub 10 and the opening 32 of each container 19 faces upward. The rack 40 secures each container 19 in a suspended, upright position so that the solution 50 is easily inserted into the opening 32 of the proximal end 30 of the container 19.

In the case of a syringe, the syringe 20 is loaded into the rack 40 in the tub 10, so that the distal end 26 (See FIG. 2) of the syringe barrel 22, covered by the syringe cap 28 (See FIG. 2), faces the bottom 12 of the tub 10 and the proximal end 30 of the syringe barrel 22, into which the plunger 35 fits, faces upward. When more than one syringe 20 containing the solution 50 of active agent is being lyophilized concurrently, the plurality of syringes 20 are loaded into the rack 40 in the tub 10.

In one option, the container 19 (e.g., syringe 20) is filled with the solution 50 before being loaded into the rack 40 in the tub 10. In another option, the container 19 (e.g., syringe 20) is loaded into the rack 40 and placed in the tub 10 first before being filled with the solution 50. It should also be understood that if multiple containers 19 (e.g., syringes 20) are lyophilized simultaneously, the multiple containers 19 in one option, are filled with the solution 50 before being loaded into the rack 40 in the tub 10 and in another option, the multiple containers 19 are filled with the solution 50 after being loaded into the rack 40 in the tub 10.

Figure 5:
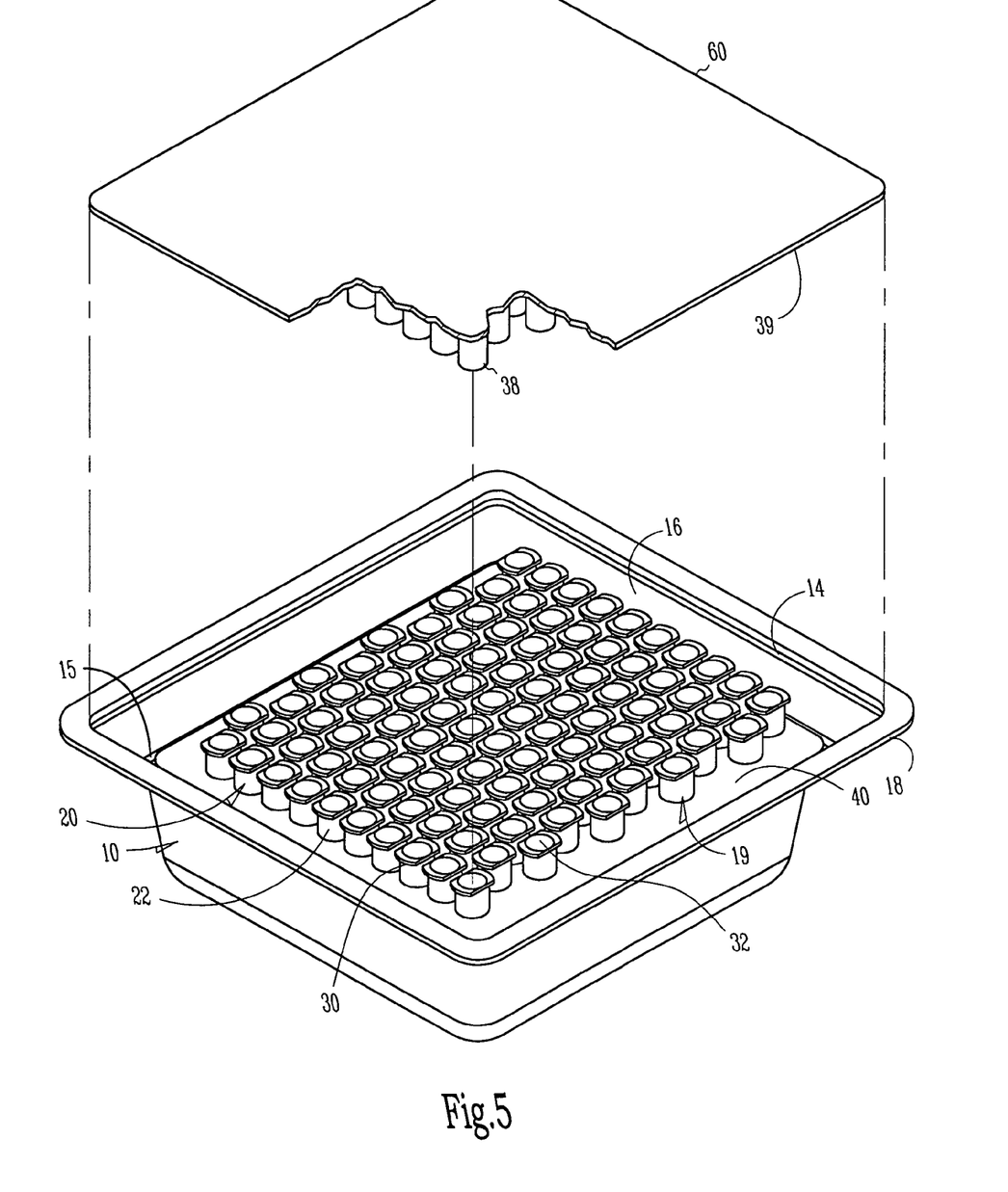
FIG. 5 is a partial cut-away view of a covering plate aligned over a plurality of suspended syringes in a tub as provided in accordance with one embodiment.

FIG. 5 illustrates another embodiment where a covering plate 60 is placed on the first ledge 14 extending around the inside 16 periphery of the top 18 of the tub 10 and includes one or more closed covering plate protuberances 38 on a surface to align with an opening 32 of at least one container 19. The user positions the covering plate 60 having an underside 39 surface which includes at least one closed protuberance 38 that projects from the underside 39 surface and aligns with at least one container 19. The one or more protuberances 38 that project from the underside surface 39 of the covering plate 60 are adapted to fit inside a portion of the one or more containers 19. The covering plate protuberance 38 includes a variety of shapes adapted to fit inside the opening 32 of the container 19 (e.g., conical, spherical, cylindrical) In one example, the covering plate 60 is a lid of substantially planar shape and includes multiple closed covering plate protuberances 38 used to cover the opening 32 of multiple containers 19 (e.g., syringes 20) after the solution 50 is deposited therein (See FIG. 4).

In one option, the removable rack 40 sits on the second ledge 15 in the tub 10 and secures each removable syringe 20 in a suspended upright position such that the opening 32 of the proximal end 30 of each syringe 20 faces toward the top 18 of the tub 10. The closed covering plate protuberance 38 is attached to the underside 39 of the covering plate 60 and adapted to fit inside the opening 32 of the syringe barrel 22 of the syringe 20. In one embodiment, a plurality of closed covering plate protuberances 38 are attached to the underside 39 of the covering plate 60 and are adapted to fit inside the opening 32 of the syringe barrel 22 of each syringe 20. The covering plate 60 acts as a lid for the top 18 of the tub 10.

The covering plate 60 acts as a lid and, in one example, includes a closed circular covering plate protuberance 38 which fits inside the opening 32 of the container 19 (e.g., syringe 20), fitting so as to allow the passage of vapor from the containers 19 but securely enough to prevent the escape of lyophilizate during lyophilization. In another example, the covering plate 60 includes an array of the covering plate protuberances 38, so as to be used during the lyophilization of multiple containers 19 (e.g., syringes 20) simultaneously. The covering plate 60 essentially forms a cap over the opening 32 of each container 19 and a lid over the tub 10. It should be understood that the covering plate 60 includes a variety of shapes (e.g., square, rectangular, circular) adapted to fit on the first ledge 14 on the inside 16 periphery of the top 18 of the tub 10 into which the container 19 is loaded, as long as the covering plate 60 caps the container 19.

During lyophilization, any lyophilizate that contacts the covering plate 60 is retained thereon. Lyophilization is performed to isolate a relatively small amount of active agent for its ultimate application, and thus, if any amount of active agent leaves a container 19 (e.g. syringe 20) and is captured on the covering plate 60 covering the container 19, the amount of lyophilized active agent remaining in the container 19 is unknown. Thus, any container 19 losing any lyophilzate captured by the covering plate 60 must be discarded.

One function of the covering plate 60 is to allow the escape of vapor from the container 19 during lyophilization, while preventing escape of the lyophilizate. In addition to identifying any container 19 (e.g. syringe 20) which loses lyophilized active agent captured by the covering plate 60 during lyophilization, the covering plate 60 prevents contamination of lyophilzate of one container 19 by the lyophilizate from another container 19 when multiple containers 19 are lyophilized simultaneously in close proximity.

Figure 6:
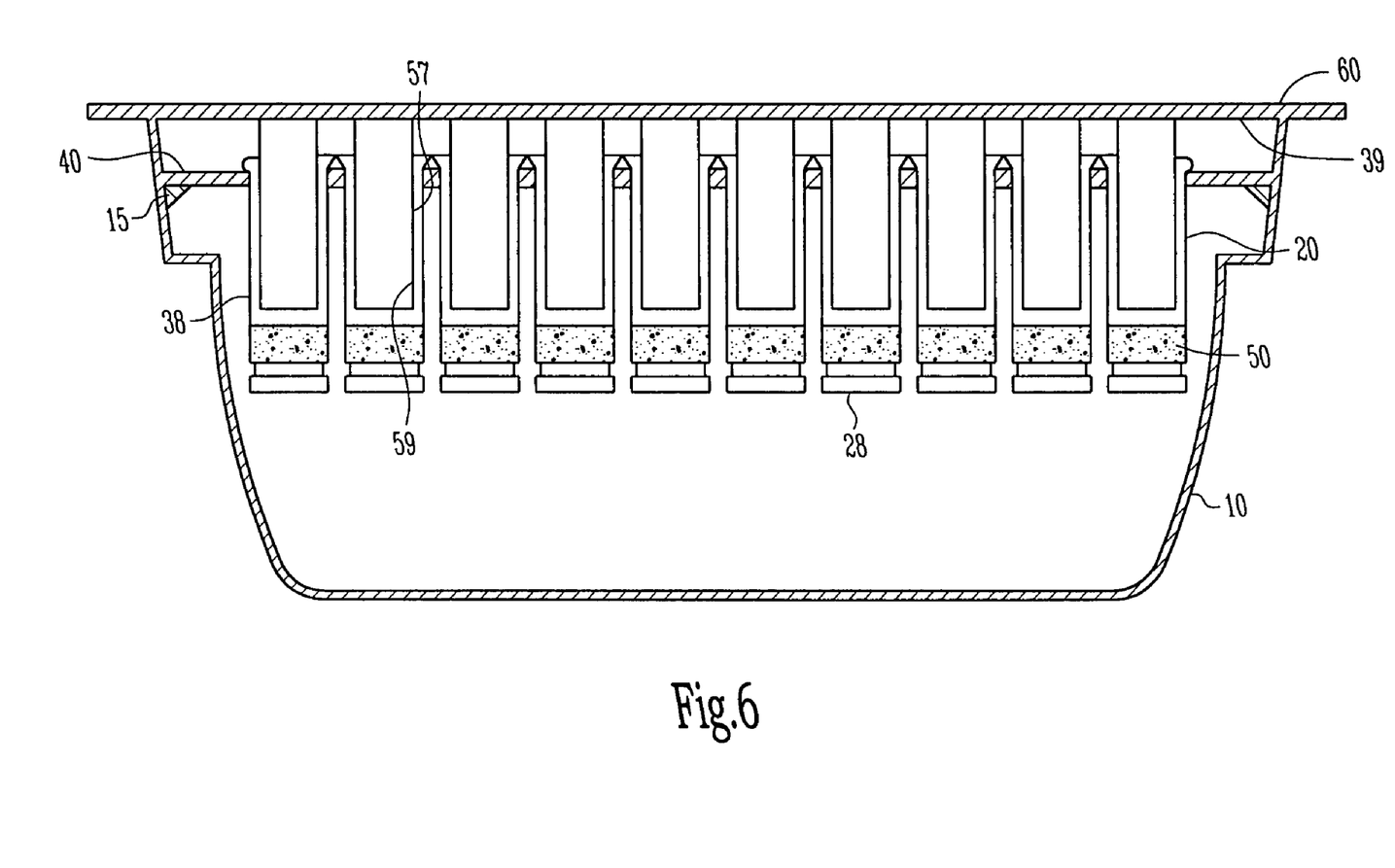
FIG. 6 is a cross-sectional view of a plurality of suspended syringes in a tub and covered by a covering plate as provided in accordance to one embodiment.

FIG. 6 illustrates one embodiment of the covering plate 10 covering multiple containers 19 with the covering plate 60. Multiple covering plate protuberances 38 engage inside the portion of multiple delivery containers 19. In one option, the covering plate protuberances 38 are positioned so that the entire length of each covering plate protuberance 38 is within the interior wall 90 of each container 19. In another option, the covering plate protuberances 38 are positioned so that at least a portion of the length of each covering plate protuberance 38 is within the interior wall 90 of the containers 19. In yet another option, each covering plate protuberance 38 includes a tapered portion adapted to fit within the interior wall 90 of each container 19.

Figure 7:
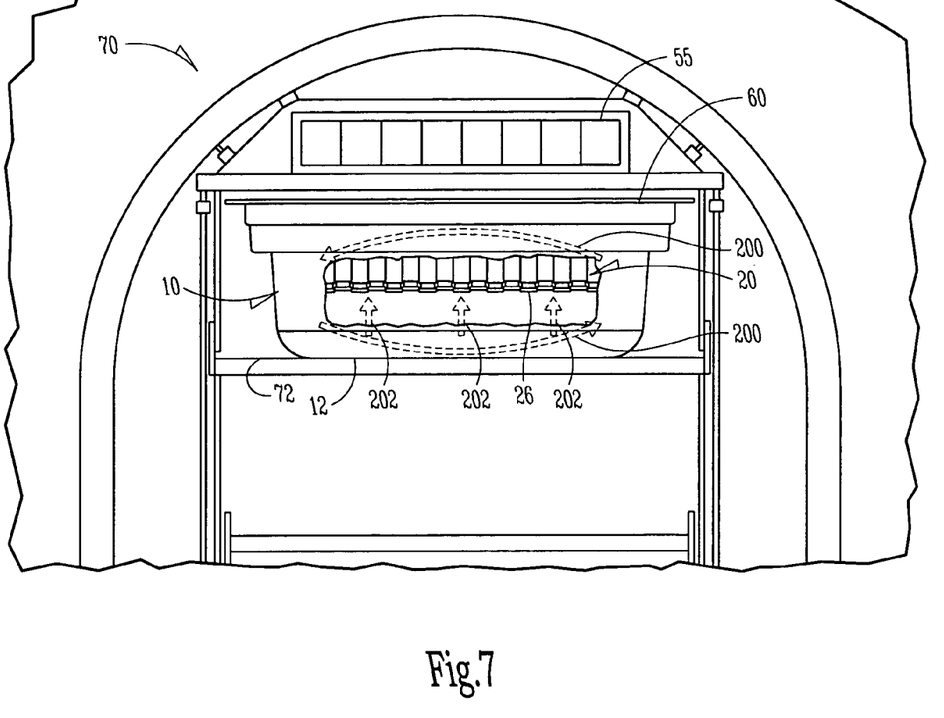
FIG. 7 is a frontal, partial cut-away view of a plurality of suspended syringes in a tub and covered by a covering plate inside of a lyophilizing apparatus as provided in accordance to one embodiment.

FIG. 7 illustrates the tub 10 placed on a shelf 72 inside a lyophilizing apparatus 70 with the covering plate 60 covering a plurality of containers 19. In one option, the containers 19 (e.g., syringes 20) are covered with the covering plate 60 before placing the containers (e.g., syringes 20) and the covering plate 60 inside the lyophilizing apparatus 70. In another option, the containers 19 (e.g., syringes 20) are covered with the covering plate 60 after placing the containers 19 (e.g., syringes 20) and the covering plate 60 inside the lyophilizing apparatus 70. The distal end 26 of each syringe 20 faces toward the bottom 12 of the tub 10. The bottom 12 of the tub 10 is placed on the shelf 72 of the lyophilizing apparatus 70. The lyophilization apparatus 70 is then closed, and the solution 50 (not shown) is cooled by radiation, convection or both, until the solution 50 is transformed into a frozen solid. For example, the solution 50 is cooled to a temperature between about 0° C. and −50° C. The rack 40 (See FIG. 3) inside the tub 10 suspends the syringes 20 above the surface of the bottom 12 of the tub 10 and prevents the syringes 20 from coming into contact with any cooling surface of the lyophilizing apparatus 70 (e.g., shelf 72). After cooling, a vacuum 55 is applied to the inside of the lyophilizing apparatus 70, including inside the chamber 24 of the syringe barrel 22 of each syringe 20 and outside each syringe 20 to dry the material (See FIG. 2). Lyophilizing the solution 50 or partially lyophilizing the solution 50 by cooling the solution and applying a vacuum to the solution allows vapor to escape through an annular gap 57 between each of the at least one covering plate protuberances 38 and a side wall 59 of each of the one or more containers 19. (See FIG. 6) Lyophilization by convection, radiation, or both is advantageous over lyophilization by conduction because these techniques increase economies of lyophilizing multiple containers 19 at the same time. Lyophilization by conduction occurs by placing the container containing the medication in intimate physical contact with a cooling surface of the lyophilizing apparatus 70 (e.g., shelf 72), allowing cooling to occur by heat transfer as a result of the physical contact. Lyophilization is conventionally achieved by conduction because conduction is an effective means of heat transfer.

In one embodiment, lyophilization occurs by convection 200, radiation 202, or both, to increase the ease with which a number of containers 19 are cooled simultaneously during lyophilization. Cooling by convection 200 occurs by the cooling of air being circulated around the material being cooled. Cooling by radiation 202 occurs by the emission of radiant energy in the form of waves or particles. Neither cooling by convection 200 nor by radiation 202 occurs by the physical contact of the container 19 with a cooling surface of the lyophilizing apparatus 70, and thus, cooling by these means occurs without such contact. In one embodiment, lyophilization by convection 200 radiation 202 or both is performed by suspending the container 19 (e.g. syringe 20) to be lyophilized above the cooling surface of the lyophilizing apparatus 70 (e.g., shelf 72). In one option, the container 19 is suspended by the rack 40 within the tub 10 and placed within the lyophilizing apparatus 70.

The cooling step makes the process of the invention easier to perform and generally more user-friendly than lyophilization cooling by conduction. Whereas lyophilization by conduction requires manually placing each container 19 onto the cooling shelf 72 of the lyophilizing apparatus 70, lyophilization in one option is performed by simply loading each container 19 into the tub 10 which is in turn placed into the lyophilizing apparatus 70, allowing for the lyophilization of multiple containers 19 with one simple step. This greatly increases the economies of lyophilization by the invention over that of lyophilization by conduction.

Cooling by convection, radiation or both can take longer than cooling by conduction. However, the cooling time of the solution 50 is not prohibitively long, and the efficiencies realized by cooling the solution 50 with respect to the above embodiments can outweigh the increased cooling time.

After the solution 50 is cooled to a frozen solid, the vacuum 55 is applied to the lyophilizing apparatus 70 to provide at least a partial vacuum within the container 19 and outside of the container 19 but still within the lyophilizing apparatus 70. The vacuum 55 is applied to the solution 50 to dryness or the solution 50 is at least partially lyophilized. In one example, the water content of the lyophilized solution 50 is less than 1% water. In another example, the water content of the lyophilized solution 50 is less than 5% water. The cooling and vacuum processes are performed to remove liquid from the active agent in solution 50 at low temperature by sublimation. This process is used as opposed to other methods so as not to denature, degrade or otherwise damage the active agent by heat.

After sublimation occurs to dryness, the tub 10, container 19 (e.g. syringe 20) and covering plate 60 are removed from the lyophilization apparatus 70. The covering plate 60 is removed from the proximal end 30 of the container 19 (See FIG. 5) and examined for any retained lyophilizate. If the covering plate 60 contains any such lyophilizate, each container 19 from which the lyophilizate came is discarded.

In one option, after lyophilization of the solution 50, the opening 32 (See FIG. 5) of any undiscarded container 19 is sealed for storage and prior to usage. The container 19 is sealed with those apparatuses known for sealing container 19. For example, where the container 19 is a syringe 20, the opening 32 of the syringe barrel 22 is sealed, in one option, with the plunger 35 of the syringe 20.

In another option, the plunger tip 34 is inserted into the proximal end 30 of the syringe barrel 22 of each remaining syringe 20 (See FIG. 2). For example, with the use of the Becton Dickinson and Company "Hypak" configuration of pre-packaged syringes 20, after the covering plate 60 is removed following lyophilization, each plunger tip 34 is inserted into the syringe barrel 22 of the corresponding syringe 20 with one step. The "Hypak" arrangement provides plunger tip 34 connected to a two-dimensional grid or array, which allows the plunger tip 34 to be removed from or replaced into each barrel 22 of the corresponding syringe 20 with a single step. Each plunger rod 33 is thereafter screwed into a corresponding plunger tip 34 (See FIG. 2). This further increases the efficiency with which lyophilization according to this embodiment occurs.

Figure 8:
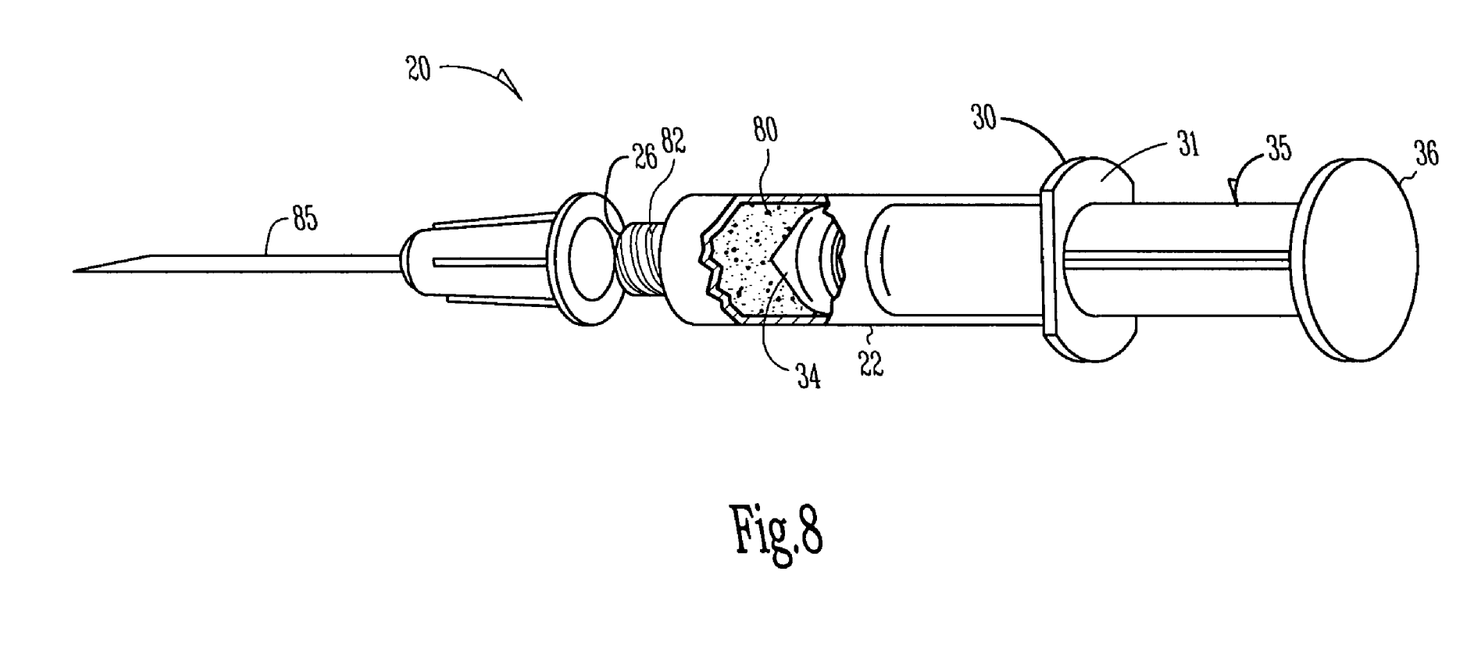
FIG. 8 is a perspective view of a syringe as provided in accordance with one embodiment.

In one embodiment, when the lyophilized medication 80 is ready for use, the seal is removed from the container 19 and diluent is added to the container 19 for reconstitution. The lyophilized active agent is then ready for use. FIG. 8 illustrates one embodiment where the delivery container 19 is a syringe 20. The syringe cap 28 (See FIG. 2) covering the distal end 26 of the syringe barrel 22 is removed, and a needle 85, cannula or other delivery mechanism is inserted into the distal end 26, for example, by screwing it onto the threaded end 82 incorporated into the distal end 26 of the syringe barrel 22. The needle 85 of the syringe 20 is then inserted into a receptacle containing the diluent, and the plunger 35 of the syringe 20 is withdrawn towards the proximal end 30 of the syringe barrel 22 by pulling the plunger head 36 of the plunger 35 away from the syringe flange 31, until the appropriate amount of diluent is extracted into the syringe 20 for reconstitution. The syringe 20 is withdrawn from the diluent-containing receptacle, and the contents of the syringe 20 are mixed by agitation until the lyophilized medication 80 is dissolved or suspended in the diluent. The reconstituted active agent is now ready for administration.

Reconstitution of a lyophilized medication 80 also occurs by instantaneous dissolution, agitation, or passing the lyophilizate/diluent mixture between two syringes 20 until a homogenous suspension is achieved. The dissolved or suspended contents are administered from the syringe 20 to a patient through the needle 85, cannula or other delivery mechanism.

Figure 9:
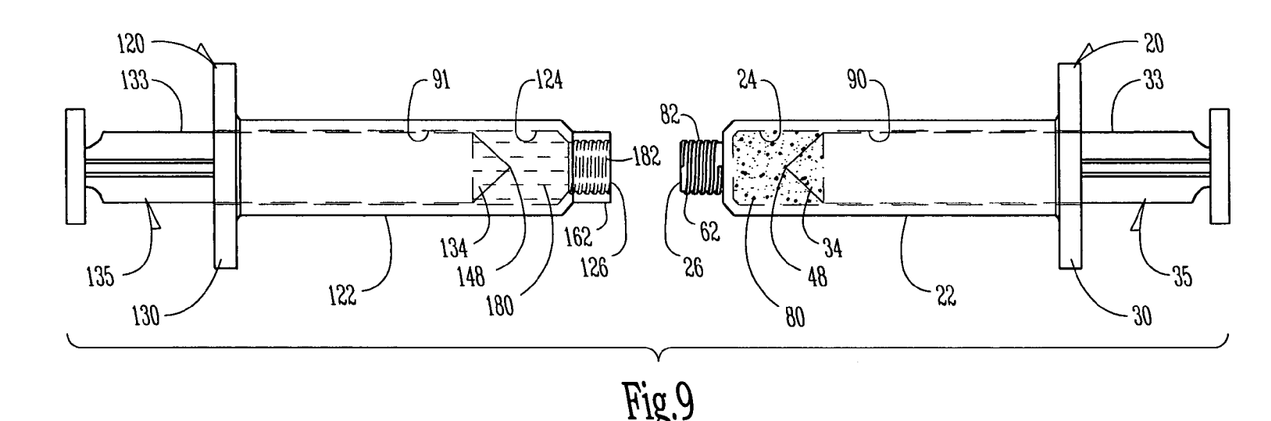
FIG. 9 is a side view of two syringes as provided in accordance with one embodiment.

FIG. 9 illustrates another embodiment of reconstituting the lyophilized medication 80. A first syringe 20 includes a first syringe barrel 22 having an open proximal end 30, a distal end 26, and a substantially cylindrical interior wall 90 of a chamber 24 extending therebetween. A first plunger 35 includes a plunger rod 33 connected to a first plunger tip 34 extending towards the distal end 26 of the first syringe barrel 22. The cylindrical interior wall 90 of the chamber 24 encompasses the first plunger tip 34 slidably positioned for maintaining fluid tight engagement with the first cylindrical interior wall 90 of the chamber 24.

In one option, a lyophilized medication 80 introduced into the chamber 24 of the first syringe barrel 22 is displaced between the distal end 26 of the first syringe barrel 22 and a distal end 48 of the first plunger tip 34 to maintain sterility of the lyophilized medication 80. Distal end 26 of the first syringe barrel 22 includes a male luer-lock fitting 62 which extends axially therethrough and communicates with the chamber 24 of the syringe barrel 22. The male luer-lock fitting 62 is a threaded end 82. A syringe cap 28 (see, FIG. 2) is inserted over the male luer-lock fitting 62 of the first syringe barrel 22 during packaging to maintain sterility of the lyophilized medication 80 of the first syringe 20.

A second syringe 120 includes a second syringe barrel 122 having an open proximal end 130, a distal end 126, and a substantially cylindrical interior wall 91 of a chamber 124 extending therebetween. A second plunger 135 includes a plunger rod 133 connected to a second plunger tip 134 extending towards the distal end 126 of the second syringe barrel 122. The cylindrical interior wall 91 of the chamber 124 encompasses the second plunger tip 134 slidably positioned for maintaining fluid tight engagement with the cylindrical interior wall 91 of the chamber 124.

In one option, a solution 180 (e.g., a diluent) is introduced into the chamber 124 and displaced between the distal end 126 of second syringe barrel 122 and a distal end 148 of the second plunger tip 134 to maintain sterility of the solution 180 (e.g., a diluent). The distal end 126 of the second syringe barrel 122 includes a female luer-lock fitting 162 which extends axially therethrough and communicates with the chamber 124 of the syringe barrel 122. The female luer-lock fitting 162 is a threaded receiving end 182. A second syringe cap (not shown) is inserted over the female luer-lock fitting 162 of the second syringe barrel 122 during packaging to maintain sterility of the solution 180 (e.g., a diluent) of the second syringe barrel 122.

Figure 10:
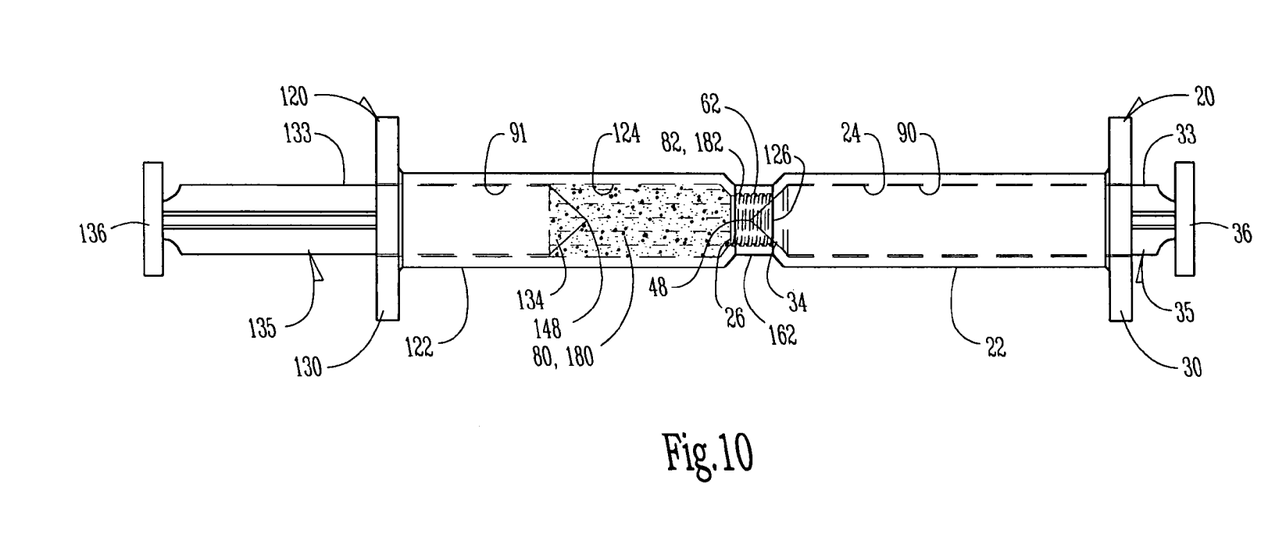
FIG. 10 is a side view of two interlocked syringes as provided in accordance with one embodiment.

FIG. 10 illustrates another embodiment where the first syringe 20 disengageably interlocked with the second syringe 120. Specifically, the syringe cap 28 (see, FIG. 2) is removed from the male luer-lock fitting 62 revealing threaded end 82 of the first syringe barrel 22 and the second syringe cap (not shown) is be removed from the female luer-lock fitting 162 revealing threaded receiving end 182 of the second syringe barrel 122. The threaded end 82 of the male luer-lock fitting 62 of the first syringe barrel 22 is mated with the threaded receiving end 182 of the female luer-lock fitting 162 of the second syringe barrel 122 by connecting the threaded end 82 of the male luer-lock fitting 62 with the threaded receiving end 182 of the female luer-lock fitting 162 and turning the threaded end 82, the threaded receiving end 182, or both in a locked position for fluid tight engagement.

Once the first syringe 20 is interlocked with the second syringe 120, the lyophilized medication 80 located at the distal end 26 of the first syringe barrel 22 is fluidly mixed with the solution 180 (e.g. a diluent) located at the distal end 126 of the second syringe barrel 122. Mixture of the lyophilized medication 80 and solution 180 is achieved by the alternating fluid tight movement of the first plunger tip 34 by the first plunger 35 sliding along the first cylindrical interior wall 90 of the first syringe barrel 22 and the second plunger tip 134 by the second plunger 135 sliding along the cylindrical interior wall 91 of the second syringe barrel 122.

The alternating fluid tight movement between the chamber 24 of the first syringe barrel 22 and the chamber 124 of the second syringe barrel 122 is achieved by pushing a plunger head 136 of the second plunger rod 133 which forcibly pushes the distal end 148 of the interconnected second plunger tip 134 along the cylindrical interior wall 91 toward the distal end 126 of the second syringe barrel 122. The sliding motion of the second plunger 135 toward the distal end 126 of the second syringe barrel 122 forces the solution 180 (e.g., a diluent) from the chamber 124 of the second syringe barrel 122 and forcibly through to the chamber 24 of the first syringe barrel 22. The pushing of the solution 180 by the second plunger tip 134 from the chamber 124 of the second syringe barrel 122 into the chamber 24 of the first syringe barrel 22 forcibly pushes the first plunger tip 34 back toward the proximal end 30 of the first syringe barrel 22 pushing the first plunger 35 distally and away from the proximal end 30 of the first syringe barrel 22.

Subsequently pushing a plunger head 36 of the first plunger rod 33 which forcibly pushes the distal end 48 of the interconnected first plunger tip 34 along the cylindrical interior wall 90 toward the distal end 26 of the first syringe barrel 22. The sliding motion of the first plunger tip 34 toward the distal end 26 of the first syringe barrel 22 forces the mixed medication (i.e., the lyophilized medication 80 and solution 180) from chamber 24 of the first syringe barrel 22 back through to the chamber 124 of the second syringe barrel 122. The pushing of the mixed medication (i.e., the lyophilized medication 80 and solution 180) by the first plunger 35 along the cylindrical interior wall 90 of the first syringe barrel 22 into the second syringe barrel 122 forcibly pushes the second plunger tip 134 back toward the proximal end 130 of the second hollow barrel 122 pushing the second plunger 135 distally and away from the proximal end 130 of the second syringe barrel 122. The rotation of pushing and pulling the first plunger 35 of the first syringe 20 and the subsequent pushing and pulling the second plunger 135 of the second syringe 120 is repeated for uniform mixture of the medication.

EXAMPLE

An example of the use of one embodiment is the lyophilization of leuprolide acetate by the process of this embodiment. A solution 50 containing approximately 38 mg/ml of leuprolide acetate in water is prepared by mixing the leuprolide acetate in water until dissolved. A tub 10 of syringes 20 is opened so the opening 32 of the proximal end 30 of each syringe 20 is exposed. Approximately 0.3 milliliters of leuprolide acetate solution is filled into each syringe 20 by means of a pipette through the opening 32 of the proximal end 30 of each syringe 20. When all of the syringes 20 are filled with the drug solution 50, the tub 10 containing the plurality of syringes 20 is placed on the shelf 72 of the lyophilizing apparatus 70. The syringes 20 are then covered with the covering plate 60. The shelf 72 of the lyophilizing apparatus 70 includes a refrigerant circulating within the shelf 72 to control temperature. The temperature of the shelf 72 is reduced to approximately −50° C. until the solution 50 in each syringe 20 is frozen well below 0° C. by radiant and/or convectant cooling. The vacuum 55 is applied to the chamber and the shelf 72 temperature is slowly raised to room temperature until the water in the syringes 20 is removed by sublimation. The result is a lyophilized powder in each syringe 20 of approximately 11.4 milligrams.

The tub 10 is removed from the lyophilizing apparatus 70. The covering plate 60 is removed from the opening 32 of the syringes 20. Each area of the covering plate 60 is examined for captured lyophilizate and the syringes 20 from which any such captured lyophilizate came are discarded. Plunger tips 34 are installed into the opening 32 of the proximal end 30 of the syringes 20, and plunger rods 33 are screwed into the corresponding plunger tips 34 The syringes 20 are now ready for reconstitution.

Active Agent

Active agent includes any therapeutically-active agent, and possible excipient, that is lyophilized. Excipients tend to increase the stability and the ease of suspension and reconstitution of therapeutically-active agents for and during lyophilization. An exemplary category of excipient includes ionic and non-ionic (amphoteric) surfactants, specific examples of which include polysorbates, cremophores and tyloxopols. Another type of exemplary excipient includes bulking agents, specific examples of which include sodium and potassium phosphates, citric acid, tartaric acid, gelatins, and carbohydrates such as dextrose, mannitol and dextran. An additional type of exemplary excipient is lyoprotectants, including glucose, catalase, maltose, maltotriose and maltohexose.

Examples of therapeutically-active agents include substances capable of prevention an infection systemically in an animal or human, or locally at the defect site, for example, antibacterial agents such as penicillin, cephalosporins, bacitracin, tetracycline, doxycycline, gentamycin, quinolines, neomycin, clindamycin, kanamycin, and metronidazole; anti-inflammatory agents such as hydrocortisone, and prednisone; antiparasitic agent such as quinacrine, chloroquine, and vidarbine; antifungal agents such as nystatin; antiviral agents such as acyclovir, ribarivin, and interferons; analgesic agents such is salicylic acid, acetaminophen, ibuprofen, naproxen, piroxicam, flurbiprofen, and morphine; local anesthetics such as cocaine, lidocaine, bupivacaine and benzocaine; immunogens (vaccines) for simulating antibodies against hepatitis, influenza, measles, rubella, tetanus, polio, and rabies; peptides such as leuprolide acetate (an LH-RH agonist), nafarelin, ganirelix, and goserelin.

Substances, or metabolic precursors thereof, which are capable of promoting growth and survival of cells and tissues or augmenting the functioning of cells are also used, for example, as a nerve growth promoting substance, such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-α), transforming growth factor-β (TGF-β), epidermal growth factor (EGF), fibroblast growth factor (FGF), interleukin-1 (IL-1), and prostaglandins such as $PGE_1$, $PGE_2$ and $PGD_2$; an osteoinductive agent or bone growth promoting substance such a bone chips or demineralized bone material; and antineoplastic agents such as methotrexate, 5-fluouracil, adriamycin, vinblastine, cisplatin, tumor-specific antibodies conjugated to toxins, and tumor necrosis factor.

Other active agents include hormones such as progesterone, testosterone, follicle simulating hormone (FSH) (used for birth control and fertility-enhancement), insulin, and somatotrophins; antihistamines such as diphenhydramine and chlorphencramine; cardiovascular agents such as digitalis, nitroglycerine, papaverine and streptokinase; anti-ulcer agents such as cimetidine hydrochloride, and isopropamide iodide; bronchodilators such as metaproternal sulfate and aminophylline; vasodilators such as theophylline, niacin and minoxidil; central nervous system agents such as tranquilizer, b-adrenergic blocking agents, and dopamine; antipsychotic agents such as risperidone and olanzapine; narcotic antagonists such as naltrexone, naloxone and buprenorphine.

Additional examples of active agents are provided in U.S. Pat. No. 5,234,529, the disclosure of which is incorporated by reference herein.

Container

The container 19 includes any receptacle in which an active agent is lyophilized, reconstituted and ultimately used.

An exemplary delivery container 19 is the syringe 20. Although the use of glass vials or ampules for lyophilization is quite common, the use of the syringe 20 for lyophilization is uncommon. The syringe 20, however, is the preferable means for lyophilization for active agents whose ultimate use will be from a syringe 20, since the active agent is used, for example, for its ultimate application after reconstitution in the syringe 20 in which it was lyophilized. Lyophilization in a vial or ampule, on the other hand, requires transfer of the reconstituted active agent from the vial or ampule to the syringe 20. The syringe 20 is useful, for example, for lyophilizing injectable medications, since the medications are ultimately administered in the syringe 20.

Plastic syringes 20, as opposed to glass syringes 20, are the preferable containers 19, since plastic syringes 20 are the drug delivery vehicle of choice for injectable medications. Glass syringes 20 are susceptible to breakage and are more fragile than plastic syringes 20. Alternatively, plastic syringes 20 are stronger, and thus, safer for health care professionals to use both in reconstituting and administering injectable medications. Plastic syringes 20 are also lighter and cheaper than glass syringes 20.

In addition, the bore size of commercially-available glass syringes 20 typically is quite small, requiring a greater amount of force to use the syringe 20 than with a larger bore size. Because plastic is stronger than glass, the bore size of the plastic syringes 20 is, in one option, larger than those of comparable glass syringes 20, decreasing the force required to use the syringe 20.

Plastic for syringes 20 is generally lighter, cheaper and stronger than glass. Plastic syringes 20 are also cheaper to manufacture than glass syringes 20, further adding to the advantages of the invention.

What is claimed is:

1. A method for lyophilizing a solution, the method comprising:

removably loading one or more containers into a tub;

depositing the solution into the one or more containers;

positioning a covering plate comprising one or more protuberances projecting from an underside surface thereof to align with an opening of the one or more containers, the one or more protuberances adapted to fit inside without contacting at least a portion of the one or more containers;

covering the one or more containers with the covering plate before placing the tub and the covering plate inside a lyophilizing apparatus or covering the one or more containers with the covering plate after placing the tub and the covering plate inside the lyophilizing apparatus, the one or more protuberances engaged inside the portion of the one or more containers;

at least partially lyophilizing the solution by cooling the solution and applying a vacuum to the solution, wherein at least partially lyophilizing the solution allows vapor to escape through an annular gap between each of the one or more protuberances and a side wall of each of the one or more containers; and removing the covering plate from the one or more containers after the lyophilization of the solution.

2. The method of claim 1, further comprising examining the underside surface of the covering plate for retained lyophilizate and discarding the one or more containers from which the lyophilizate came.

3. The method of claim 1, wherein removably loading the one or more containers comprises removably loading one or more containers into a rack and suspending the rack within the tub, the rack adapted to suspend the one or more containers in the tub.

4. The method of claim 3, wherein suspending the rack within the tub comprises preventing the one or more containers from coming into contact with a cooling source of the lyophilizing apparatus.

5. The method of claim 4, wherein preventing the one or more containers from coming into contact with the cooling source comprises preventing the one or more containers from coming into contact with a cooling shelf of the lyophilizing apparatus.

6. The method of claim 3, wherein removably loading the one or more containers into the rack comprises securing each container in a suspended upright position such that the opening of each container faces toward a top of the tub.

7. The method of claim 1, wherein depositing the solution into the one or more containers comprises depositing the solution into one or more syringes.

8. The method of claim 1, wherein covering the one or more containers with the covering plate comprises forming a lid preventing the escape of lyophilizate from the one or more containers during the lyophilization process.

9. The method of claim 1, wherein covering the one or more containers with the covering plate comprises preventing contamination of lyophilizate from one container by the lyophilizate from another container when two or more containers are lyophilized simultaneously.

10. The method of claim 1, wherein cooling the solution comprises cooling the solution by convection.

11. The method of claim 1, wherein cooling the solution comprises cooing the solution by radiation.

12. The method of claim 1, wherein cooling the solution comprises cooling the solution by convection and radiation.

13. The method of claim 1, wherein cooling the solution comprises cooling the solution to a temperature between about 0° C. and −50° C.

14. The method of claim 1, wherein lyophilizing the solution comprises producing about 11.4 mg of lyophilizate in each container.

15. The method of claim 1, further comprising sealing the one or more containers containing the at least partially lyophilized solution.

16. The method of claim 15, wherein sealing the one or more containers comprises inserting a plunger into each opening of one or more syringes.

17. The method of claim 15, further comprising reconstituting the at least partially lyophilized solution, including adding a diluent to the one or more containers.

18. The method of claim 17, further comprising coupling a needle or cannula to a distal end of the one or more containers.

19. The method of claim 1, wherein removably loading the one or more containers into the tub comprises removably loading a plurality of syringes into a rack and suspending the rack within the tub.

\* \* \* \* \*

UNITED STATES PATENT AND TRADEMARK OFFICE
CERTIFICATE OF CORRECTION

PATENT NO. : 7,467,482 B2
APPLICATION NO. : 11/099919
DATED : December 23, 2008
INVENTOR(S) : Yarborough et al.

It is certified that error appears in the above-identified patent and that said Letters Patent is hereby corrected as shown below:

On page 2, under "Other Publications", in column 2, line 5, delete "Resonse" and insert -- Response --, therefor.

On page 2, under "Other Publications", in column 2, line 7, delete "Respone" and insert -- Response --, therefor.

In column 6, line 47, delete "lyophilzate" and insert -- lyophilizate --, therefor.

In column 6, line 55, delete "lyophilzate" and insert -- lyophilizate --, therefor.

In column 7, lines 33-43, delete "Lyophilization by convection, radiation, or both is advantageous over lyophilization by conduction because these techniques increase economies of lyophilizing multiple containers 19 at the same time. Lyophilization by conduction occurs by placing the container containing the medication in intimate physical contact with a cooling surface of the lyophilizing apparatus 70 (e.g., shelf 72), allowing cooling to occur by heat transfer as a result of the physical contact. Lyophilization is conventionally achieved by conduction because conduction is an effective means of heat transfer." and insert the same on Col. 7, Line 34, below "(See FIG. 6)" as a new paragraph.

Signed and Sealed this

Thirty-first Day of March, 2009

JOHN DOLL
*Acting Director of the United States Patent and Trademark Office*